US009028251B2

(12) United States Patent
Walsh et al.

(10) Patent No.: US 9,028,251 B2
(45) Date of Patent: May 12, 2015

(54) ILLUMINATING DENTAL INSTRUMENT, COUPLING AND METHOD OF USE

(75) Inventors: Laurence J. Walsh, Queensland (AU); Michael Nicholas Mandikos, Queensland (AU)

(73) Assignees: Topstore Pty Ltd, Queensland (AU); LJ Walsh Dental Pty Ltd, Queensland (AU)

(*) Notice: Subject to any disclaimer, the term of this patent is extended or adjusted under 35 U.S.C. 154(b) by 0 days.

(21) Appl. No.: 13/497,770

(22) PCT Filed: Sep. 21, 2010

(86) PCT No.: PCT/AU2010/001238
§ 371 (c)(1),
(2), (4) Date: May 21, 2012

(87) PCT Pub. No.: WO2011/035372
PCT Pub. Date: Mar. 31, 2011

(65) Prior Publication Data
US 2012/0219924 A1 Aug. 30, 2012

Related U.S. Application Data

(60) Provisional application No. 61/244,558, filed on Sep. 22, 2009.

(51) Int. Cl.
*A61C 1/08* (2006.01)
*A61C 1/18* (2006.01)

(52) U.S. Cl.
CPC .. *A61C 1/088* (2013.01); *A61C 1/18* (2013.01)

(58) Field of Classification Search
CPC ......... A61C 1/088; A61B 1/24; A61B 1/0615
USPC ........................................................ 433/29
See application file for complete search history.

(56) References Cited

U.S. PATENT DOCUMENTS 6,186,780 B1 2/2001 Hibst et al.
6,331,111 B1 * 12/2001 Cao .................................. 433/29
(Continued)

FOREIGN PATENT DOCUMENTS

DE 20304675 U1 6/2003
JP 2003305058 A 10/2003
(Continued)

OTHER PUBLICATIONS

International Search Report mailed Nov. 19, 2010 from International Application No. PCT/AU2010/001238.
(Continued)

*Primary Examiner* — Ralph Lewis
(74) *Attorney, Agent, or Firm* — Schwabe, Williamson & Wyatt (57) ABSTRACT

A dental instrument, or a coupling connectable to the dental instrument, comprises an illuminator having a plurality of light emitting diodes that are each capable of emitting light at a selected wavelength in a range 260 to 880 nm. White or near white light emitting diodes may also be included together with a switch. Fluorescence-based diagnosis can be assisted by the use of a single dye or mixture of dyes. Light of about 400-540 nm wavelength may be used to distinguish composite, porcelain or other tooth coloured filling materials from normal tooth structures. Light of about 260-450 nm wavelength may be used to identify dental caries, calculus and/or dental plaque. Light of about 350-500 nm wavelength may be used to cure dental composite. Typically, the dental instrument is, or comprises, a drill, de-scaler, or other instruments such as for cleaning, examination or diagnosis of dental conditions.

18 Claims, 4 Drawing Sheets

(56) References Cited

U.S. PATENT DOCUMENTS

| | | | |
|---|---|---|---|
| 7,029,277 B2 * | 4/2006 | Gofman et al. | 433/29 |
| 2003/0091955 A1 * | 5/2003 | Burtscher et al. | 433/29 |
| 2006/0040231 A1 * | 2/2006 | Quan et al. | 433/29 |
| 2007/0121786 A1 * | 5/2007 | Okawa et al. | 378/119 |

FOREIGN PATENT DOCUMENTS

| | | | |
|---|---|---|---|
| JP | 2004089239 A | 3/2004 | |
| WO | 01/52723 A1 | 7/2001 | |
| WO | WO02/083023 A1 | 10/2002 | |

OTHER PUBLICATIONS

Written Opinion mailed Nov. 19, 2010 from International Application No. PCT/AU2010/001238.

International Preliminary Report on Patentability mailed Jan. 11, 2012 from International Application No. PCT/AU2010/001238.

* cited by examiner

ILLUMINATING DENTAL INSTRUMENT, COUPLING AND METHOD OF USE

CROSS REFERENCE TO RELATED APPLICATIONS

The present application is a U.S. National Stage of International Patent Application No. PCT/AU2010/001238, filed Sept. 21, 2010, entitled "Illuminating Dental Instrument, Coupling And Method Of Use," and which claims the benefit of U.S. Provisional Patent Application No. 61/244,558, filed Sept. 22, 2009, the entire content and disclosure of which are hereby incorporated by reference in its entirety.

FIELD

THIS INVENTION relates to dentistry. More particularly, this invention relates to a dental instrument and/or coupling therefor, that provides illumination during drilling, descaling, examination, restoration and other dental procedures.

BACKGROUND

Much attention has been applied in the recent past to improving the appearance of tooth coloured filling materials, with a wide range of composite resin and porcelain filling materials now available. The aim has been to make these restorative dental filling materials as similar in appearance to tooth structure as possible. The intention is that when a tooth is fractured (traumatically), decayed, severely worn or otherwise damaged, then composite resin and porcelain filling materials with their corresponding adhesives, may be used to restore the tooth to its pre-damaged state. A primary goal has thus been to make the filling "invisible" so that once restored, the tooth appears to be intact, as the restoration is difficult to see visually.

As a result, filling materials have evolved to the point whereby they mimic tooth structure in terms of opacity, hue and chromaticity. In the case of some of the higher end composite and porcelain materials available, these restoratives will also provide some fluorescence and opalescence properties as well. At the present time, it is possible to restore a badly broken down tooth with multiple layers of varying coloured composite filling materials, such that it is very difficult to distinguish between natural tooth structure and the prosthetic material. Porcelain restorations manufactured by a skilled dental ceramist can also be very difficult to distinguish from natural tooth structure.

However, dental restorations do not last indefinitely, and eventually all composite and porcelain materials begin to wear, break down, leak at their margins or lose their shine and become discoloured. Accordingly, there is a need to remove and/or replace composite and porcelain fillings from teeth. A major concern for the clinician is that the process of removing a filling will result in more tooth structure being ground away and hence more damage occurring to the tooth. With the increasing use of tooth-coloured fillings, which can replicate the optical properties of natural tooth structure, it can be extremely difficult to be certain that no such fillings have escaped recognition or have been misidentified during a clinical examination or when removing an existing filling to access underlying decay. Such fillings are not unambiguously visible. Differences in fluorescence provide such a method for identifying tooth coloured fillings. Tooth-coloured restorative materials, dental caries and calculus have a different fluorescence signature from healthy tooth structure.

In the case of modern composite and porcelain filling materials, the overall match in shade between the remaining natural tooth structure and the filling material may be very good, making it difficult to distinguish between restorative material and remaining enamel and dentine. There is the very real risk that excessive tooth structure will be cut or ground away from the natural tooth during removal of an existing filling. The consequence is that the residual tooth will become weaker and may even suffer damage to its pulp (nerve). Additionally, the time it takes a clinician to continuously stop, dry and visualise the remaining tooth-filling interface, increases the length of time needed to perform the procedure and hence the appointments become longer or greatly rushed. There is also the potential problem of not visualising all of the remaining old filling material in the tooth, and hence leaving some behind. This in turn may result in bacteria remaining in the tooth after the new restoration is placed or may compromise bond strengths of the new filling that is subsequently placed, and both of these events may cause further problems post-operatively.

Fluorescence can be used in the detection of fillings because the light-induced fluorescence signals from tooth coloured fillings differ from those for normal dental enamel. The fluorescence emission properties of healthy dental enamel were characterized by Angmar-Mansson and others at the Karolinska Institute in the late 1980's and early 1990s. Visible blue light (470 nm) was shown to elicit yellow fluorescence from the calcium-phosphate bonds in hydroxyapatite. (Sundstrom et al., 1985, Swed Dent J. 9:71-80; Angmar-Mansson et al., 1996, Eur J Oral Sci. 104: 480-485) Previous work on fluorescence identification of tooth coloured fillings has used separate external light sources (Stimpson 1985, Acta Med Leg Soc (Liege) 35:278-284. Pretty et al., 2002, J Forensic Sci. 47:831-6) rather than a diagnostic light which is incorporated into a device for cutting or cleaning, as in the current invention.

Another major problem facing the dental clinician relates to caries (decay) in a tooth, either in the form of a new lesion, or recurrent caries beneath a previously placed composite, porcelain or other restoration. Recurrent decay beneath existing fillings poses a particular problem in that any excessive removal of tooth tissue weakens the remaining tooth structure and makes injury to the dental pulp more likely. In order to treat the tooth, the dentist must visualise all of the decay to facilitate its mechanical debridement with a dental handpiece and bur, or with another type of cutting technology, such as a diamond coated tip in an ultrasonic handpiece. The technique that is employed under local anaesthetic is to visualise the discoloured tooth structure, assume it is decay (either by its visualised colour or by tactile feel), and then the tooth is ground with the bur to remove this infected dentine. However, under normal lighting conditions, decayed dentine does not always appear significantly different to the surrounding sound tooth structure, and tactile probing to determine the extent of decay can be very subjective. A very real risk exists that an overly zealous technique may be applied by the dental clinician and that too much tooth structure will be removed in the operative process. This will weaken the tooth and may lead to pulp complications as previously described. Alternatively, and perhaps worse, it is also possible that not all of the decayed tooth structure will be identified by the dentist, and that some decay may be left behind by not removing enough tooth structure before the new filling is placed. A method which can assist the dental clinician in determining that infected dentine still remains will result in more conservative tooth cavity preparations.

Tooth decay can proceed at varying rates in different individuals and decay that is deep and rapidly advancing may be difficult to fully detect by normal visual and tactile methods alone. Using dental X-rays can assist in detecting the presence of decay beneath fillings, but this method cannot assist the dental clinician during the procedure, once the filling has been removed and they are then faced with the decision regarding how much natural tooth tissue to remove in the various areas of the cavity. Accordingly, other aides have been used by the clinician to determine the boundary between sound tooth structure and infected diseased structure, so that only the latter is removed. Colour, disclosing dyes, tactile feel, laser light and short wavelength light fluorescence, and resistance to the drill are all techniques that are used.

One example, "Carisolv", is a chemical solution based on sodium hypochlorite with amino acids which attacks that part of the tooth which is decayed. The net result is that demineralised parts of the tooth are softened and a dedicated bur is then used to selectively remove the decayed tooth structure, hopefully without damage to the deeper, sound parts of the tooth.

Another approach has been to use a caries (decay) detection dye based on basic fuchsin or acid red dyes. This material is applied to the tooth and will stain caries tissue red and make its appearance distinct from the surrounding tooth. This technique is not particularly specific and may lead to more tooth structure being removed than is necessary. In some instances, red dye will remain in the tooth after the procedure, which may in turn leave a pink hue to the finished filling.

The process of fluorescence occurs when incident light applied to a structure is emitted at a longer wavelength, with some conversion of the incident energy into heat. The process of fluorescence has been exploited for a range of diagnostic methods, for example the detection of hidden fissure caries by the DiagnoDENT device, in which visible red laser light (655 nm wavelength) elicits fluorescence in the near infrared region (700-900 nm). Because bacterial products such as porphyrins evoke the fluorescence, the intensity of the emitted light is related to the volume of the carious lesion. Similar fluorescence processes occur with porphyrins in dental calculus, where ultraviolet light elicits red fluorescence, and visible red light elicits near infrared emissions. This process is best termed POSITIVE fluorescence, in that the desired target (in this case the caries or dental calculus) elicits the fluorescence signal.

Laser-light based technologies such as the "Diagno-Dent" have been used to measure the near infrared fluorescence signal of bacteria present in the tooth, identifying regions that do not fluoresce strongly in a manner consistent with sound dentine. This device can be used as a diagnostic tool to identify subsurface areas of a tooth where decay is occurring, but cannot be seen from the surface. Following on from this concept, the application of short wavelength light via a dedicated, stand-alone instrument such as the "Sopro Aceon" have also been proposed as a means of illuminating a decayed tooth and stimulating fluorescence of the decayed region. The differential fluorescence between diseased and healthy tooth structure then assists the clinician to distinguish between boundaries in the tooth, allowing more careful removal of only the decayed tooth structure, leaving the sound part of the tooth alone. For light wavelengths from 400 to 420 nm, carious lesions with cavitations in dentine containing bacteria show emissions at 600-700 nm typical for porphyrin compounds (Buchalla, 2005, Caries Res. 39:150-6). The bacteria and their metabolic products induces an increase in the absorption in the UVA and visible blue spectral region from 350-420 nm, which results in the appearance of a fluorescence signal in the visible red spectral region at 590-650 nm (Borisiva et al., 2006, Lasers Med Sci. 21:34-41).

Yet another problem that exists pertains to the thorough and complete removal of dental plaque and calculus (tartar) from teeth during a scale and cleaning hygiene appointment. Whilst older, mature calculus that has been on the teeth for a long time may begin to become dark in colour and is readily visible, newer plaque and calculus deposits, as well as the remnants of large deposits that may have been incompletely scaled off the teeth, are often light in colour, frequently matching the shade of the teeth themselves. This can make it very difficult to adequately visualise the bacterial deposits that need to be removed from the teeth. As ultrasonic scaling techniques are performed with a copious water spray, visualisation of the field of cleaning can be compromised, leading to insufficient removal of the plaque and calculus.

This problem can be overcome in part by frequently stopping the ultrasonic scaling procedure and thoroughly drying the teeth, in an attempt to observe the remaining plaque and calculus, as this will dry to a "frosty" or "sandy" appearance relative to the shiny natural tooth structure. However, it is often difficult to completely dry the teeth in all parts of the mouth, and this also takes time and draws out the appointment duration. A more ready means of identifying the plaque and calculus on the teeth at the time of debridement would be preferred.

As mentioned previously, a disclosing dye may be applied to the teeth prior to scaling and cleaning. The plaque and calculus will then stain pink or red.

However, this can lead to excessive staining of the mouth and lips as a whole and is not a technique that is preferred by patients. An alternative approach is to use the concept of fluorescence of bacterial plaque and calculus and hence shining a light of specific wavelength directly onto the teeth to be cleaned. This causes red fluorescence of the bacterial deposits, helping the clinician to identify their location, prior to cleaning. However, this technique requires the frequent and repeated stopping of the scaling process and shining of the light on the teeth in order to have some efficacy. This is an inconvenient process and also contributes to considerable time delays in the scaling and cleaning appointment.

The ultraviolet and visible blue wavelengths are desirable for fluorescence diagnosis. Under UVA excitation (363.8 nm), enamel has a fluorescence spectrum which has the shape of a wide band, with a maximum of 450 nm (characteristic of a blue-green shade) and a slow decrease up to 680 nm. The enamel fluorescence does not depend on the colour of the tooth. Dentine has a distribution spectrum which is similar to that of enamel but is three times fuller. The spectra of dental porcelains comprises a wide band due to transition metals, and fine lines due to rare earth elements (terbium and europium). When the saturation degree of the ceramic increases, its fluorescence colour varies due to the relative increase in the amplitude of the lines in relation to the bands. Thus, when the porcelain colour is more saturated, its fluorescence colour becomes greener (Stimpson et al., 1985, supra).

With regard to identifying deposits of dental plaque or dental calculus, under UVA and visible blue light, positive red fluorescence from deposits of mature dental plaque on the surface of teeth, restorations, or dental appliances can be identified. This can be done to assist in their controlled removal by a powered scaler, as well as being used as an aid in oral hygiene education. Following tooth cleaning, residual deposits of plaque and calculus appear as red fluorescing areas (Kühnisch et al., 2003, Int Poster J Dent Oral Med 5: 177). Red fluorescence is associated with mature dental plaque on dentures. The maturity of dental plaque, rather than the presence of cariogenic streptococci, is the basis for the red fluorescence (Coulthwaite et al., 2006, Caries Res. 40:112-6).

Many of the aforementioned analytical and examination techniques available to dentists, and other techniques, are reviewed in Walsh, 2008, Australasian Dental Practice 19 47.

SUMMARY

A limitation of prior art dental illuminators such as hereinbefore described is that they are "stand-alone" devices that must be used separately from other dental instruments such as drills, scalers and polishers. This can create practical difficulties for the dentist who has to use two separate devices (i.e illuminator and dental instrument) for examining teeth and performing dental procedures such as removing old tooth coloured filling materials (such as composite resin or porcelain restorations), removing plaque, buffing or polishing teeth and curing dental composite material.

The present invention is therefore broadly directed to a dental instrument, or a coupling therefor, comprising an illuminator that is capable of emitting light of a plurality of selectable wavelengths. The illuminator may be in the dental instrument, or may be in a separate coupling operatively connectable to the dental instrument. The wavelength of emitted light may be selected for particular diagnostic purposes and/or for curing dental composite.

In one aspect, the invention provides a coupling for a dental instrument, said coupling comprising an illuminator that comprises a plurality of light emitting elements that are each capable of emitting light at a selected wavelength for transmission to said dental instrument.

Suitably, the coupling is releasably connectable to the dental instrument.

In one embodiment, the coupling comprises a mating portion that is releasably, operatively connectable to a mating portion of the dental instrument. Suitably, according to this embodiment the coupling comprises a plurality of conduits that are releasably connectable to respective conduits in said dental instrument. Said plurality of conduits may comprise one or more water, air, electrical and/or optical conduits connectable to one or more water, air, electrical and/or optical conduits in said dental instrument.

In another embodiment, the coupling comprises a fibre-optic conduit releasably mountable to the dental instrument. In use, the fibre-optic conduit emits light transmitted from the coupling.

In another aspect, the invention provides a dental instrument operatively connected to the coupling of the aforementioned aspect.

In yet another aspect, the invention provides a dental instrument comprising an illuminator that comprises a plurality of light emitting elements that are each capable of emitting light at a selected wavelength.

Suitably, in use the illuminator provides sufficient light for the dental instrument to illuminate an oral cavity and/or a dental structure in the oral cavity.

In yet another aspect, the invention provides a method of performing a dental procedure on a patient, said method including the step of using a dental a dental instrument according to the aforementioned aspects to perform the dental procedure.

In still yet another aspect, the invention provides a method of dental examination of a patient, said method including the step of using a dental instrument according to the aforementioned aspects to perform the dental examination.

Preferably, the illuminator further comprises one or more light emitting elements capable of emitting white, or near white, light.

Suitably, said plurality of light emitting elements are each capable of emitting light at a selected wavelength in a range 260 to 880 nm.

Examples of particular wavelengths within this range include 300 nm, 350 nm, 380 nm, 400 nm, 420 nm, 450 nm, 465 nm, 500 nm, 540 nm, 600 nm, 650 nm, 680 nm, 700 nm, 750 nm and 800 nm and any ranges between any of these wavelengths.

Preferably, at least one of said plurality of light emitting elements is capable of emitting light at a selected wavelength in a range selected from the group consisting of:
(i) 260 to 450 nm.
(ii) 400 to 700 nm; and
(iii) 400 to 540 nm.

In one particular embodiment, light of about 400 to 540 nm wavelength is used to distinguish composite, porcelain or other tooth coloured filling materials from normal tooth structure such as enamel or dentine.

In another particular embodiment, light of about 260 to 450 nm wavelength is used to identify dental caries and/or calculus and dental plaque.

In yet another particular embodiment, light of about 350 to 500 nm wavelength is used for curing or photo-polymerizing a dental composite.

In a particularly preferred form of the abovementioned aspects, the light emitting elements comprise light-emitting diodes (LEDs).

In one particular form, the one or more light emitting elements capable of emitting white, or near white, light may be a white-emitting LED or may be a combination of green, red and blue LEDs.

Suitably, the dental instrument and/or coupling further comprises a switch for selecting between said light emitting element capable of emitting white, or near white, light and/or between said light emitting elements that are capable of emitting light at a selected wavelength.

In preferred embodiments, the dental instrument is, or comprises, an instrument for inspection, examination, visualization, diagnosis, burnishing, polishing, drilling, scaling, curing or photo-polymerizing dental composite, tooth extraction or other aspects of dentistry.

In a particularly preferred embodiment, the dental instrument is a drill or de-scaler.

In certain embodiments, fluorescence-based examination, inspection, visualization or diagnosis can be assisted by the use of a single dye or mixture of dyes. Specific dyes can be used which bind selectively to the leaking margins of existing fillings, to areas of early decay in enamel, to areas of decay on root surfaces of teeth, to deposits of plaque of calculus, or to existing types of tooth coloured filling materials. Binding of the dye alters the fluorescence emission and enhances the visual discrimination of these under illumination.

In other embodiments, methods utilizing the coupling and/or dental instrument may be facilitated by the use of one or more filters through which the user (e.g. a clinician) examines the illuminated area. These filters suppress or exclude the illuminating wavelength and pass the longer wavelength fluorescence emission so that this can be seen by the clinician. Specific examples include orange and red filters when UVA or visible blue light is produced by the illuminating source.

Preferably, the respective wavelengths emitted by the illumination source are matched to one or more long pass optical filters through which a user views an illuminated area. These filters may be attached to the dental instrument may be worn by the user (e.g. in the form of, or attached to protective eyewear or as a mask) or may be handheld as a separate device.

The invention is suitable for use in the dental treatment of humans and non-human animals.

Throughout this specification, unless the context requires otherwise, the words "comprise", "comprises" and "comprising" will be understood to imply the inclusion of a stated integer or group of integers but not the exclusion of any other integer or group of integers.

BRIEF DESCRIPTION OF THE DRAWINGS

In order that preferred embodiments of the present invention may be more readily understood and placed into practical effect, preferred embodiments of the invention will be described, by way of example only, with reference to the accompanying drawing in which:

FIGS. 1A & B shows an embodiment of a dental instrument comprising a compressed air-operated dental drill operatively connectable to a coupling;

DETAILED DESCRIPTION

Figure 1:
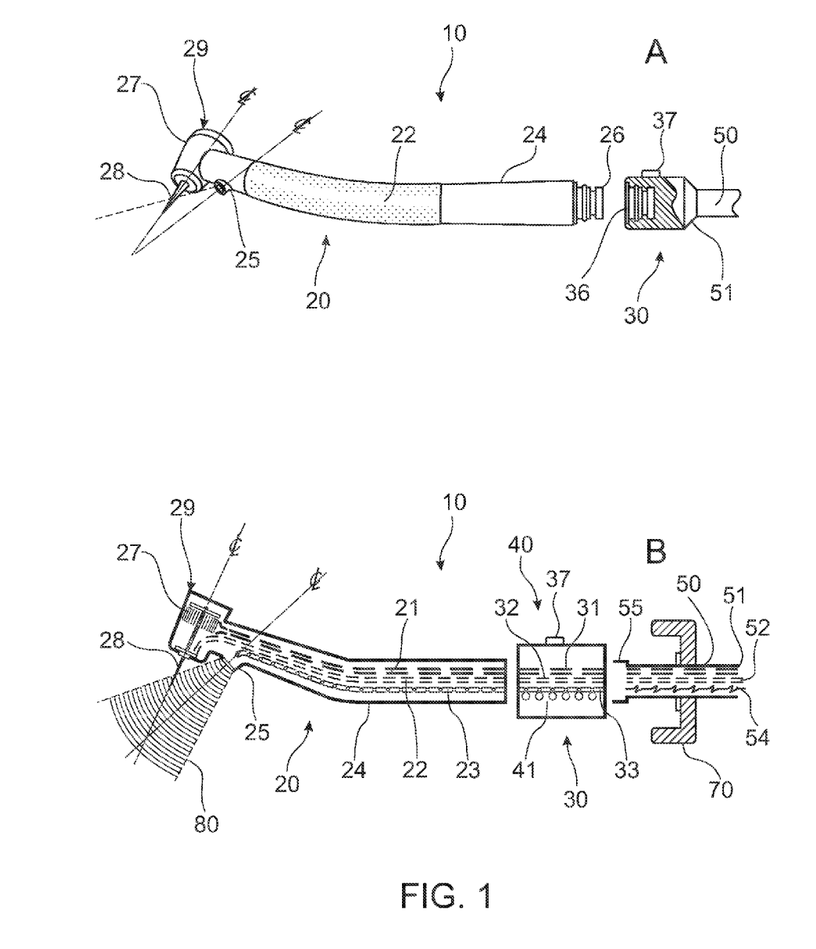

Referring to FIGS. 1A and 1B, dental instrument 10 comprises drill 20, that comprises handle 24 having grip 22, head 29 comprising drill turbine 27 and drill bit 28 and moveable lens 25. Coupling 30 includes illuminator 40 that comprises plurality of LEDs 41. Coupling 30 and dental instrument 20 are releasably, operatively connectable by way of respective mating portions 36 and 26. For convenience, coupling 30 may be retained in holder 70 which is typically provided on a dental tray (not shown). Referring particularly to FIG. 1B, coupling 30 is connectable to connector 55 of conduit housing 50 that houses separate compressed air conduit 51 and water conduit 52, which are respectively connected to sources of compressed air and water (not shown). Coupling 30 comprises air conduit 31 connectable to air conduit 51 and water conduit 32 connectable to water conduit 52. Coupling 30 further comprises fibre-optic conduit 23 which transmits light emitted by plurality of LEDs 41.

Handle 24 of drill 20 comprises compressed air conduit 21, water conduit 22 and fibre-optic conduit 23 that respectively connect to compressed air conduit 31, water conduit 32 and fibre-optic conduit 33 of coupling 30. In use, compressed air conduit 21 supplies compressed air to drive drill turbine 27 and water conduit 22 supplies water to cool the interface between drill-bit 28 and the dental structure. Moveable lens 25 is positioned in handle 24 proximal to drill-bit 28 to project illumination 80 about the centreline indicated in FIG. 1B so that illumination 80 is focussed about or near a patient's teeth or oral cavity where drilling is performed.

In this embodiment, plurality of LEDs 41 in coupling 30 are electrically powered via electrical conduit 54 in connector 55, which is connected to a source of electrical power (not shown). A switch 37 in the coupling 30 or in a base unit to which it connects allows an LED of an appropriate, specific wavelength, or a white or near white LED, to be selected.

It will also be appreciated that coupling 30 could be a "common" coupling 30 comprising compressed air conduit 31, water conduit 32, fibre-optic conduit 33 and an electrical conduit (not shown) to enable coupling 30 to be used interchangeably between electrically- and compressed air-powered dental instruments 20.

Figure 2:
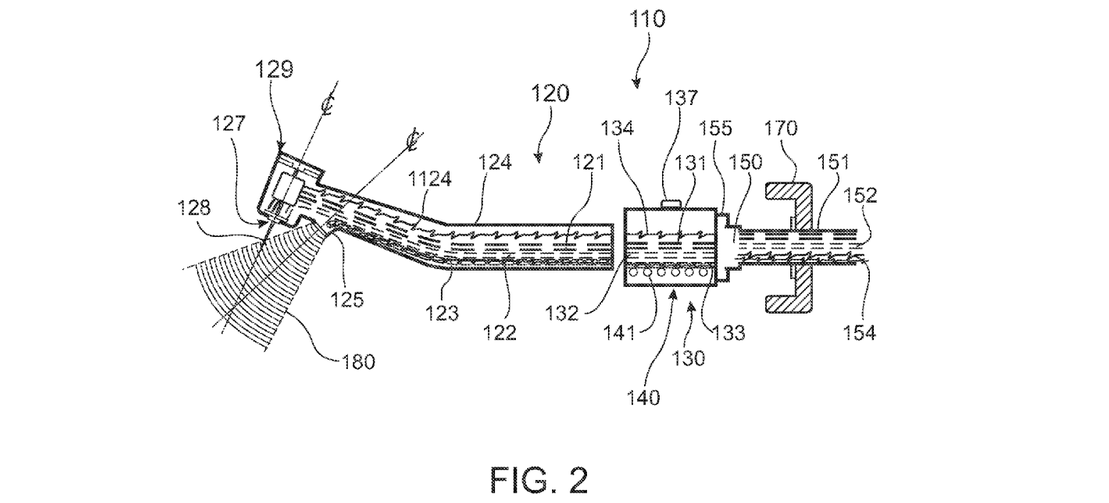
FIG. 2 shows an embodiment of a dental instrument comprising an electric-powered dental drill operatively connectable to a coupling.

Accordingly, another embodiment is shown in FIG. 2, in which dental instrument 110 is drill 120 that comprises drill bit 128 that is electrically-powered In this embodiment, electrical conduit 1124 in dental instrument 120 connects to electrical conduit 134 of coupling 130 which is connected to electrical conduit 154 of connector 155 and a power source, typically of relatively low voltage such as 6-12V (not shown). In this embodiment, both the drill motor 127 and the LEDs 141 in illuminator 140 are electrically powered. As before, a switch 137 in the coupling 130 or in the base unit to which it connects allows the appropriate LED to be selected.

Figure 3:
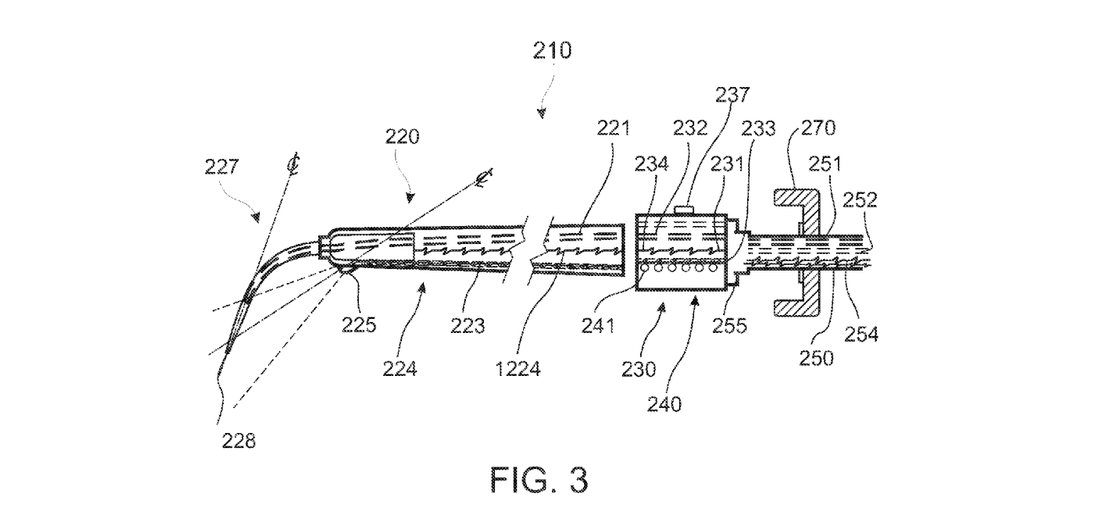
FIG. 3 shows an embodiment of a dental instrument comprising a dental de-scaler operatively connectable to a coupling.

In yet another embodiment shown in FIG. 3, dental instrument 210 is de-scaler 220 that comprises handle 224, having probe 227 with tip 228 and moveable lens 225. Coupling 230 and dental instrument 220 are releasably connectable by way of respective mating portions 236 and 226. Referring particularly to FIG. 3, coupling 230 is connected to conduit housing 250 which houses separate compressed air conduit 251 and water conduit 252, which are respectively connected to sources of compressed air and water (not shown). Coupling 230 comprises air conduit 231 connectable to air conduit 251 and water conduit 232 connectable to water conduit 252. Coupling 230 further comprises fibre-optic conduit 233 which transmits light emitted by plurality of LEDs 241 in illuminator 240 and switch 237.

Figure 4:
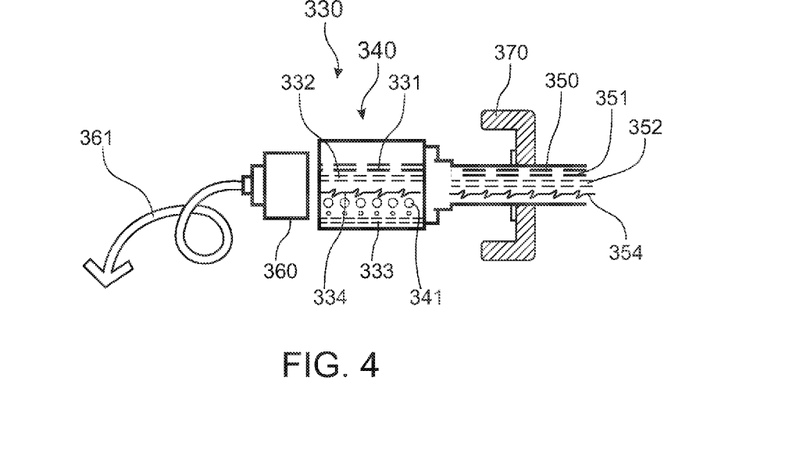
FIG. 4 shows an embodiment of a coupling and adapter for connecting a fibre-optic conduit to a dental instrument

Another particular embodiment is shown in FIG. 4, in which coupling 330 further comprises adapter 360 comprising fibre-optic conduit 361 having light output 362 which is mountable to dental instrument 320 by way of a clip or sleeve (not shown). In this embodiment, fibre-optic conduit 361 transmits light emitted by plurality of LEDs 341 in illuminator 340 located in coupling 330.

Figure 5:
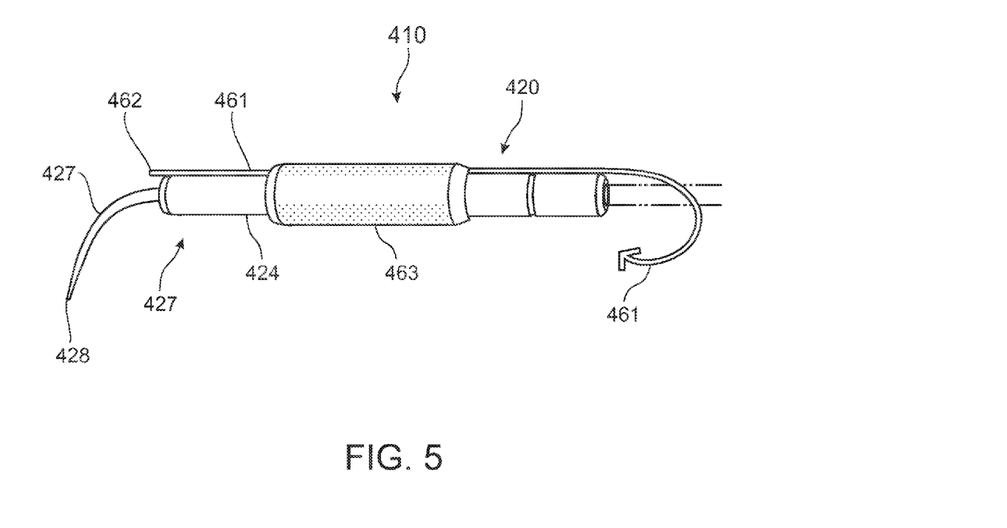
FIG. 5 shows an embodiment of a dental de-scaler having a fibre-optic conduit removably mounted thereto.

In another embodiment shown in FIG. 5, dental instrument 410 is ultrasonic de-scaler 420 comprising ultrasonic probe 427 having tip 428, wherein clip or sleeve 463 is adapted to removably mount fibre-optic conduit 461 from the adapter shown in FIG. 4, to ultrasonic scaler 420. Light output 462 of fibre-optic conduit 461 is positioned in a manner that illuminates teeth (not shown) proximal to tip 428 of ultrasonic probe 427, thereby providing suitably directed illumination during de-scaling of teeth.

Figure 6:
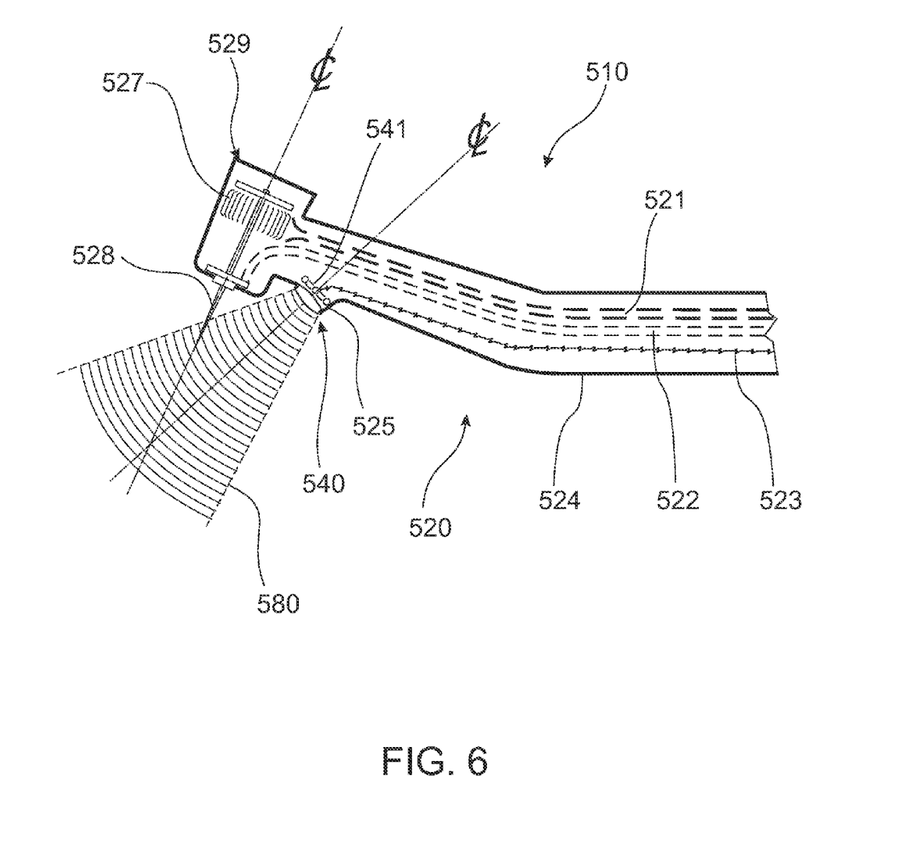
FIG. 6 shows an embodiment of a dental instrument comprising an illuminator.

In another embodiment in FIG. 6, dental instrument 510 is drill 520 that comprises illuminator 540 mounted near head 529, illuminator 540 comprising plurality of LEDs 541 with moveable lens 525. Plurality of LEDs 541 receive electrical power from electrical conduit 523 which is connected to an electrical power source (not shown). In this embodiment drill 520 comprises drill bit 528 and air-driven turbine 527 where air conduit 521 is connected to a source of compressed air (not shown). Water conduit 522 is connected to a source of water (not shown) to facilitate cooling turbine 527. Alternatively, drill 520 may be electrically powered by way of an electrical conduit connected to the electrical power source (not shown). As a further alternative, plurality of LEDs 541 could receive their power by induction generated by the rotation of air-driven turbine 527.

According to the aforementioned embodiments, illuminator 40 would typically comprise plurality of LEDs 41. LEDs may include one or more UVA, violet, red, green and/or blue LEDs and one or more white or near white LEDs. A switch (not shown) would enable an operator to select violet, red, green, blue or white or near white light, as required. Alternatively, plurality of LEDs 41 comprises one or more UVA, violet, red, green and blue LEDs in the absence of white or near white LEDs. It will be appreciated that in the absence of white or near white LEDs, a switch (not shown) would enable the one or more red, green and blue LEDs to be operated in combination to produce white or near white.

In one particular embodiment, the dental instrument 10 or coupling 30 comprises illuminator 40 with plurality of LEDs 41 that include at least one LED capable of producing light at a wavelength suitable for curing or photo-polymerizing a dental composite material. Typically, the at least one LED emits a "blue" wavelength typically in the range 350-500 nm. Dental composites may include photo-initiator molecules to facilitate photo-polymerization of the composite by irradiation with an appropriate wavelength of light. The most common photo-initiator is camphorquinone which absorbs blue light in a wavelength range between about 400 and 500 nm, with peak absorption occurring around 465 nm. Another photo-initiator is phenyl-propanedione (or PPD), which has an ability to absorb light of wavelengths less that 350 nm (near ultra-violet range) to about 470 nm, with its peak absorption occurring at 390 nm. Another even less common photo-initiator used in some dental materials is Lucerin TPO with absorption ability starting below about 350 nm, peaking at about 370 nm and ceasing to absorb light wavelengths above about 420 nm.

This particular embodiment enables a dental operator to switch the dental instrument between drilling or scaling modes and a curing or photo-polymerizing mode without the need to change instruments.

Use of the coupling 30 and/or dental instrument 10 may be facilitated by the use of one or more filters (not shown) through which the user (e.g. a clinician) examines an illuminated area of the oral cavity. Such filters suppress or exclude the illuminating wavelength and pass the longer wavelength fluorescence emission so that this can be seen by the clinician. Specific examples include orange and red filters when UVA or visible blue light is produced by the illuminating source.

These filters may be attached to the dental instrument 10, may be worn by the user (e.g. in the form of, or attachable to protective eyewear or as a mask) or may be handheld as a separate device such as a "paddle".

The present invention provides a dental instrument having a switchable LED light source in a dental handpiece or coupling, or within the head itself of the handpiece (e.g. a drill or ultrasonic de-scaler), capable of changing between an intense source of illuminating white or near-white light (for standard visualisation and operating) or into a light source of selected wavelengths for visualizing caries, plaque, calculus, tooth coloured fillings and/or natural tooth structure (such as dentine or enamel).

The present invention may be installed as a coupling on a dental chair, or alternatively, the fibre-optic coupling of existing dental chair delivery systems would be replaced with the coupling 30 described herein, which would allow the clinician to switch between light outputs as required. Alternatively, the existing light in present couplings could be replaced with a new, switchable LED light source. Either of these embodiments would enable the clinician to keep their existing handpieces and scalers, and continue to plug these into their single, new chair-mounted coupling.

In embodiments where the LED illuminator is included in a dental instrument (e.g. a drill or de-scaler without the coupling), such as shown in FIG. 6, then the clinician could eventually replace existing dental instruments over time. This would allow the clinician to continue to use existing couplings, and the new handpieces would draw power for the switchable LEDs from the existing coupling systems.

In embodiments hereinbefore described with particular reference to FIGS. 4 and 5, the illuminator may be a separate, LED light source connected to coupling 330, and "strapped-on" to an existing handpiece or scaler. The advantage of such an embodiment is that the light source could act in addition to the existing light source in the clinician's present handpiece or scaler, and would not necessitate the replacement of scalers, handpieces or couplings.

Throughout the specification, the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

The invention claimed is:

1. A coupling for a dental instrument, said coupling releasably connectable to the dental instrument and releasably connectable to a connector of a conduit housing that provides a common source of power, air and/or water, said coupling comprising a housing within which is an illuminator that emits light for transmission to said dental instrument, which illuminator comprises: (i) a plurality of light emitting elements that are capable of emitting light at respective, selected wavelengths; and (ii) one or more light emitting elements each capable of emitting white, or near white, light; wherein the coupling housing further comprises a switch for selecting (i) and/or (ii) and a plurality of conduits that comprise power, air and/or water conduits respectively connectable to power, air and/or water conduits in the conduit housing.

2. The coupling of claim 1, wherein said plurality of light emitting elements are each capable of emitting light at a selected wavelength in a range 260 to 880 nm.

3. The coupling of claim 2, wherein at least one of said plurality of light emitting elements is capable of emitting light at a selected wavelength in a range selected from the group consisting of:
   (i) 260 to 450 nm.
   (ii) 400 to 700 nm; and
   (iii) 400 to 540 nm.

4. The coupling of claim 3, which comprises one or more light emitting elements each capable of producing light at a wavelength in a range of about 260 to 450 nm for distinguishing dental caries, dental calculus or dental plaque from normal tooth structure.

5. The coupling of claim 3, which comprises one or more light emitting elements each capable of producing light at a wavelength in a range of about 400 to 540 nm for distinguishing tooth coloured fillings from normal tooth structure.

6. The coupling of claim 1, which comprises one or more light emitting elements each capable of producing light at a wavelength for curing or photo-polymerizing a dental composite.

7. The coupling of claim 6, wherein the one or more light emitting elements are each capable of producing light at a wavelength in a range of about 350 to 500 nm.

8. The coupling of claim 1, wherein the light emitting elements comprise a plurality of light-emitting diodes (LEDs).

9. The coupling of claim 1, wherein the one or more light emitting elements capable of emitting white, or near white, light is an LED.

10. The coupling of claim 1, which comprises a mating portion that is releasably, operatively connectable to a mating portion of a dental instrument.

11. The coupling of claim 1, which comprises an illuminating fibre-optic conduit releasably mountable to a dental instrument.

12. The coupling of claim 1, further comprising a mating portion releasably connectable to a complementary mating portion of the conduit housing.

13. A dental instrument comprising a coupling releasably connectable to the dental instrument and releasably connectable to a connector of a conduit housing that provides a common source of power, air and/or water, said coupling comprising a housing within which is an illuminator that emits light for transmission to said dental instrument, which illuminator comprises: (i) a plurality of light emitting elements that are capable of emitting light at respective, selected wavelengths; and (ii) one or more light emitting elements each capable of emitting white, or near white, light; wherein the coupling housing further comprises a switch for selecting (i) and/or (ii) and a plurality of conduits that comprise power, air and/or water conduits respectively connectable to power, air and/or water conduits in the conduit housing.

14. The dental instrument of claim 13, wherein the dental instrument comprises a lens for emitting light transmitted from the coupling.

15. The dental instrument of claim 13, wherein the dental instrument is a drill or de-scaler.

16. The dental instrument of claim 13, wherein the coupling and the conduit housing are releasably connected by respective complementary mating portions.

17. A method of performing a dental procedure on a patient, said method including the step of using a dental instrument comprising: a coupling releasably connected to the dental instrument and releasably connected to a connector of a conduit housing that provides a common source of power, air and/or water, said coupling comprises a coupling within which is an illuminator that emits light for transmission to said dental instrument, which illuminator comprises: (i) a plurality of light emitting elements that are capable of emitting light at respective, selected wavelengths; and (ii) one or more light emitting elements each capable of emitting white, or near white, light; wherein the coupling housing further comprises a switch for selecting (i) and/or (ii) to illuminate the oral cavity or a dental structure therein, while performing the dental procedure and a plurality of conduits that comprise power, air and/or water conduits respectively connectable to power, air and/or water conduits in the conduit housing.

18. A method of dental examination of a patient, said method including the step of using a dental instrument comprising a coupling releasably connected thereto and releasably connected to a connector of a conduit housing that provides a common source of power, air and/or water, said coupling comprises a housing within which is an illuminator that emits light for transmission to said dental instrument, which illuminator comprises: (i) a plurality of light emitting elements that are capable of emitting light at respective, selected wavelengths; and (ii) one or more light emitting elements each capable of emitting white, or near white, light; wherein the coupling housing further comprises a switch for selecting (i) and/or (ii), to illuminate the oral cavity or a dental structure therein while performing the dental examination and further comprising a plurality of conduits comprising power, air and/or water conduits respectively connectable to power, air and/or water conduits in the conduit housing.

* * * * *